(12) United States Patent
Klosowski et al.

(10) Patent No.: US 6,881,435 B2
(45) Date of Patent: Apr. 19, 2005

(54) CONSERVATION OF ORGANIC AND INORGANIC MATERIALS

(75) Inventors: Jerome Melvin Klosowski, Bay City, MI (US); Charles Wayne Smith, Bryan, TX (US); Donny Leon Hamilton, Bryan, TX (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/893,639

(22) Filed: Jul. 16, 2004

(65) Prior Publication Data

US 2005/0003096 A1 Jan. 6, 2005

Related U.S. Application Data

(60) Division of application No. 09/410,162, filed on Sep. 30, 1999, now Pat. No. 6,835,411, which is a division of application No. 09/129,296, filed on Aug. 5, 1998, now Pat. No. 6,022,589, which is a continuation-in-part of application No. 08/780,508, filed on Jan. 8, 1997, now abandoned.

(51) Int. Cl.⁷ ................................................ B05D 5/00
(52) U.S. Cl. ........................................ 427/4; 427/387
(58) Field of Search ...................... 427/4, 387

(56) References Cited

U.S. PATENT DOCUMENTS

| 4,100,129 A | * | 7/1978 | Beers .......................... 524/425 |
| 4,631,207 A | * | 12/1986 | Price .......................... 427/387 |
| 5,073,195 A | * | 12/1991 | Cuthbert et al. ............... 106/2 |
| 5,120,581 A | * | 6/1992 | Brunken et al. ............ 427/387 |
| 5,162,407 A | * | 11/1992 | Turner ........................ 524/108 |
| 5,431,952 A | * | 7/1995 | Ocello .......................... 427/4 |

FOREIGN PATENT DOCUMENTS

| EP | 747183 | * 12/1996 |
| FR | 2722724 | * 1/1996 |
| JP | 03-108600 | * 5/1991 |

* cited by examiner

*Primary Examiner*—Erma Cameron
(74) *Attorney, Agent, or Firm*—Jim L. De Cesare

(57) ABSTRACT

The use of certain siloxane and silane materials for the conservation of organic and inorganic materials. More specifically, this invention deals with a method of impregnating organic and inorganic materials with siloxanes and silanes and ultimately curing such materials to provide preservation properties to such materials. An especially significant use of the method is to preserve and conserve ancient artifacts. The curable materials are represented by silanol containing polymers crosslinked with trialkoxysilanes.

2 Claims, No Drawings

CONSERVATION OF ORGANIC AND INORGANIC MATERIALS

CROSS REFERENCE TO RELATED APPLICATIONS

This application is a division of application Ser. No. 09/410,162, filed Sep. 30, 1999 now U.S. Pat. No. 6,835,411, which is a division of application Ser. No. 09/129,296, filed Aug. 5, 1998 now U.S. Pat. No. 6,022,589, which is a continuation-in-part of application Ser. No. 08/780,508, filed Jan. 8, 1997 now abandoned.

This invention relates to the use of certain siloxane and silane materials for the conservation of organic and inorganic materials. More specifically, this invention deals with a method of impregnating organic and inorganic materials with siloxanes and silanes and ultimately curing such materials to provide preservation properties to such materials. An especially significant use of the method is to preserve and conserve ancient artifacts.

Plastination and/or conservation are terms that are often used in this art to denote the preservation of perishable biological specimens, especially soft, putrifiable materials with high water content. During the plastination method, water, and part or all of the fat (if present), are replaced by a curable resin system or elastomer system in order to optimize the preservation of the materials and to optimize the natural appearance of the material or enhance its aesthetic appearance.

Plastination is utilized therefore, in the preservation of whole body organs and bones, both animal and human, for pathological and anatomical studies; in zoology for the plastination of small animals, such as beetles, spiders, frogs, and reptiles, such as turtles, salamanders; in botany, for fungus and higher plant specimens; archeology for the preservation of wood, ceramics, pottery, glass, leather, jewelry, and the like.

Preservation techniques have also been used in the treating of books, newspapers, photographs and materials of a like nature.

BACKGROUND OF THE INVENTION

Plastination utilizes many different curable materials, for example, polyepoxides, polyesters, silicone rubbers, and the like. The inventors herein are aware of several patents which show the use of certain materials for plastination processes.

For example, U.S. Pat. No. 2,106,261, which issued Jan. 25, 1938 to Weidemann deals with a process in which the specimen which is to be treated is immersed in bleach. The specimen is then washed with water to remove essentially all of the bleach and the specimen is set in a dehydrating solution of alcohols, acetone or combinations thereof. Finally, the specimen is dried and coated with a clear lacquer to impregnate or encapsulate the specimen. There is no clear definition of the make up of the clear lacquer.

U.S. Pat. No. 4,205,059 which issued on May 27, 1980 to Von Hagens uses a more elaborate process in which the process starts out with the replacement of the water content of the specimen, in this case, animal or vegetable tissue, with an organic solvent which is volatile in a vacuum and at ambient temperature. Then, the specimen, which contains solvent, is held in contact with a fluid precursor polymer system in a vacuum and at a specified temperature until the solvent is volatilized and replaced in the specimen by the polymeric system. The curable system is stated as being capable of being polymerized into a solid, water insoluble, synthetic resin. The specimen to then subjected to a "drying down" time in which the excess polymeric system is allowed to flow by gravity from the specimen. The specimen is then held under polymerization conditions until the resin is cured. Claim 6 of that reference discloses that the resin is "a silicone rubber". The curable silicone rubber was described as a fully compounded curable material.

U.S. Pat. No. 2,244,992 which issued Jan. 13, 1981 to Von Hagens is a divisional of the aforementioned U.S. patent and therefore does not need additional discussion herein.

U.S. Pat. No. 4,278,701 which issued Jul. 14, 1981 to van Hagens, disclaimed the '059 patent, and the subject matter therein is the same as the '059 patent except that it does not disclose the "ambient temperature" limitation of the '059 patent.

U.S. Pat. No. 4,320,157 which issued Mar. 16, 1982 is directed to a method of converting cut sections of bio tissue into examinable plastinated sheet by a method which includes pre-treating to render the specimen suitable for impregnation, thereafter, impregnating with a fluid precursor, compressing the specimen between two parallel panels, filling the resulting formation with impregnating fluid, curing the fluid and removing the plates.

THE INVENTION

This invention deals with new and novel methods of conserving and preserving organic and inorganic materials through the use of novel processes not heretofore found in the prior art.

With more specificity, this invention deals in one embodiment with a method of conserving organic and inorganic materials, wherein the method comprises (I) impregnating a material selected from (a.) organic materials and (b.) inorganic materials with a curable polymeric system comprising (i) a siloxane polymer or a mixture of siloxane polymers having an average of at least two silanol groups per molecule and (ii) sufficient crosslinker or a mixture of crosslinkers to crosslink a significant portion of the siloxane polymer or mixture of siloxane polymers (i), and thereafter, (II) exposing the product of (I) to a catalyst or a mixture of catalysts for a time sufficient to initiate the cure of the product of (I), wherein the crosslinkers are selected from the group consisting of hydrolyzable silanes having the formula RSi(OR')$_3$ wherein R is selected from the phenyl group, hydrogen, vinyl, or an alkyl group having from 1 to 12 carbon atoms and R' is selected from hydrogen, vinyl, or an alkyl group having from 1 to 8 carbon atoms.

Yet another embodiment is a method in which the product of (II) is subjected to a treatment to cure the curable system formed by the siloxane polymer and the crosslinker of this method.

Still further, another embodiment of this invention is a method of preserving organic and inorganic materials, the method comprising a step (I) in which a material selected from (a.) organic materials and (b.) inorganic materials, is impregnated with a crosslinker or a mixture of crosslinkers sufficient to crosslink a significant portion of a siloxane polymer or a mixture of siloxane polymers having an average of at least two silanol groups per molecule; (II) thereafter, impregnating the product of (I) with siloxane polymer or a mixture of siloxane polymers having an average of at least two silanol groups per molecule, and (III) thereafter, exposing the product of (II) to a catalyst or a mixture of catalysts for a time sufficient to initiate curing of the product of (II).

As in the first embodiment, this process can be extended to include a step to cure the product of (II).

Another embodiment of this invention is a method of preserving organic and inorganic materials, wherein the method comprises (I) impregnating a material selected from (a.) organic materials and (b.) inorganic materials with a siloxane polymer or a mixture of siloxane polymers having an average of at least two silanol groups per molecule and (II) thereafter, impregnating the product of (I) with a crosslinker or a mixture of crosslinkers sufficient to crosslink a significant portion of the siloxane polymer or a mixture of siloxane polymers having an average of at least two silanol groups per molecule. Thereafter, (III), exposing the product of (II) to a catalyst or a mixture of catalysts for a time sufficient to initiate curing of the product of (II).

As before, an additional step can be used which subjects the specimen, that is treated by this method, to a curing step.

Turning to another embodiment of this invention, it has been discovered that the method embodied in the first embodiment can be modified to a method of preserving organic and inorganic materials, wherein the method comprises (I) impregnating a material selected from organic materials and inorganic materials with a cyclosiloxane or a mixture of cyclosiloxanes having an average of at least two silane hydrogens per molecule and thereafter, exposing the product created thereby to a catalyst or a mixture of catalysts for a time sufficient to initiate curing of the product. As before, an additional step can be used which subjects the specimen, that is treated by this method, to a curing step.

Still further, an embodiment of this invention is the substitution of essentially linear methylhydrogen siloxanes for the cyclic siloxanes of the method just supra and such a method preserves organic and inorganic materials using a non-cyclic siloxane or a mixture of non-cyclic siloxanes having an average of at least two silane hydrogens per molecule and having a molecular weight of 5000 g/mole or less, and thereafter, exposing the product obtained thereby to a catalyst or a mixture of catalysts for a time sufficient to initiate curing of the product. Once again, it should be apparent to those skilled in the art upon a close reading of this specification that a further step of curing the product can be utilized in this method.

A further embodiment of this invention is a method of preserving organic and inorganic materials wherein the method comprises impregnating a material selected from organic materials and inorganic materials with a siloxane polymer or a mixture of siloxane polymers having an average of at least two silanol groups per molecule and thereafter, exposing the product obtained thereby to a catalyst or a mixture of catalysts for a time sufficient to initiate curing of the product of (I) and if desired, completing the method with a curing step.

There is also a unique method embodied within this invention which is a method of preserving organic and inorganic materials, in which the method comprises impregnating a material selected from organic materials and inorganic materials with a hydrolyzable silane or a mixture of hydrolyzable silanes and thereafter, exposing the product obtained thereby to a catalyst or a mixture of catalysts for a time sufficient to initiate curing of the product and then, if desired, completing the method by curing the product. Preferred for this unique method is the crosslinker tetraethylorthosilicate. Further, this method can be additionally modified by the use of alkoxysilanes in conjunction with the orthosilicate, which alkoxy silanes, or mixtures of alkoxysilanes have the general formula $R_a Si(OR')_{4-a}$ wherein R is selected from the phenyl group, hydrogen, vinyl, or an alkyl group having from 1 to 12 carbon atoms, R' is selected from hydrogen, vinyl, or an alkyl group having from 1 to 8 carbon atoms and, a has a value of 1 or 2.

A further embodiment of the use of hydrolyzable silanes is a curable polymeric system comprising (i) a siloxane polymer or a mixture of siloxane polymers having an average of at least two silanol groups per molecule and (ii) sufficient crosslinker to crosslink a significant portion of the siloxane polymer or mixture of siloxane polymers (i), and thereafter, curing the product of (I), wherein the crosslinker is selected from a group consisting of $R''Si(Oxime)_3$ and $R''Si(Oxime)_4$ wherein R'' is selected from the phenyl group, hydrogen, vinyl, or an alkyl group having from 1 to 12 carbon atoms.

Yet another embodiment of this invention is a method of preserving organic and inorganic materials, in which the method comprises impregnating a material selected from organic materials and inorganic materials with (i) a siloxane polymer or a mixture of siloxane polymers having an average of at least two unsaturated groups per molecule; (ii) sufficient crosslinker or a mixture of crosslinkers to crosslink a significant portion of the siloxane polymer or mixture of siloxane polymers (i) wherein the crosslinker or crosslinkers are comprised of organosilicon compounds having at least two hydrogen atoms per silicon and are selected from the group consisting of (a) silanes, (b) siloxanes and (c) mixtures of (a) and (b) and, (iii) a platinum catalyst, and thereafter, (II) allowing the product of (I) to cure.

Finally, there is disclosed a method of configuring wood products, which method comprises (I) impregnating the wood product with a curable system and thereafter (II) configuring the wood product to a desired shape and (III), while maintaining the wood product in the configuration of (II), curing the curable system.

With respect to the inventive method herein, the term "negative pressure" means without pressure and essentially in a vacuum, while the term "positive pressure" denotes the absence of a vacuum. The examples herein describe negative pressure in inches of mercury and generally, 3 to 5 inches is a poor vacuum and thirty inches is considered to be a good vacuum.

The substrates utilized in the method of this invention are first subjected to a dehydration step in which any water in the substrate is displaced, or is essentially displaced by a solvent or the like.

The general method used herein was a modified method of the method used by those skilled in the art. In general, samples were first dehydrated in acetone which was contained in a freezer mounted vacuum chamber (hereinafter "FMVC"). After dehydration, the samples were placed into the materials for impregnation, such materials being set forth in detail in the following examples. Each of the samples was treated by the impregnating material for a period of several hours as noted in the examples. The process can be found in detail with regard to Example 1 below.

The siloxanes used in these examples are the following unless otherwise noted in the example:

Siloxane 1=a siloxane having an average of two vinyl groups per molecule, essentially on the terminal ends of the molecule and having dimethylsiloxy units, said dimethylsiloxy units having a degree of polymerization of about 100.

Siloxane 2=a siloxane having an average of two hydroxy groups (silanol groups) per molecule, essentially on the terminal ends of the molecule and having dimethylsiloxy units, said dimethylsiloxy units having a degree of polymerization of about 100.

Siloxane 3=a hydroxy terminated siloxane as in Siloxane 2 except its degree of polymerization is about 3 to 5.

Siloxane 4=a hydroxy terminated siloxane as in Siloxane 2 except its degree of polymerization is about 35 to 40.

Siloxane 5=a hydroxy terminated siloxane as in Siloxane 2 except its degree of polymerization is about 6 to 10.

Siloxane 6=a hydroxy terminated siloxane as in Siloxane 2 except its degree of polymerization is about 300.

EXAMPLE 1

Preservation of Artifacts: Corn Cobs

A large corn cob specimen recovered from the 1870 provenance of excavations at the Yorktown, Pa. site was selected for this experiment.

Prior to treatment, the cob was stored in a glass jar in a mixture of alcohol and water to prevent crumbling during handling. The core area of the cob was completely hollow and although there was a great deal of debris and exfoliation in the alcohol/water solution, the cob was soft to the touch and did not crumble when handled.

The cob was removed from the alcohol/water solution and rinsed for one hour in a free-running gentle bath of fresh water as a means of removing sediment and debris from the surfaces of the cob. The cob was then placed on paper towels and allowed to drain of excess surface water for two minutes before it was weighed and measured. In addition to weighing the cob, measurements of the cob were recorded for the longest points along the length of the sample as well as the mid-section diameter point of the cob. The wet weight of the cob was 16.8 grams and the sample measured 5.6 centimeters in length and 2.63 centimeters in width.

Before treatment, the cob was placed in an initial bath of acetone, which had been stored at the same temperature as the solution in which the cob had been stored, to prevent additional stress on the sample. The beaker containing the acetone and cob was then placed in a freezer mounted vacuum chamber and for six hours, a vacuum of 26.5 Psi was applied. The cessation of rapid bubbling indicated that the cob had lost essentially all of the water originally present therein. At this point, the acetone was replaced with fresh acetone that had also been stored in the freezer. The cob was allowed to sit in this solution in the freezer for twelve hours prior to impregnation.

After allowing free-running acetone to drain from the sample for less than one minute, the cob was placed in a clean, dry beaker and freezer cold polydimethylsiloxane fluid having hydroxyl groups on each end of the molecule and having a molecular weight of 350 g/mole was added to the beaker to submerge the cob thereunder. The cob was slightly buoyant in nature and therefore, the cob was arrested beneath the surface of the silicone fluid using a fine mesh wire screen. With the screen in place, the beaker was placed in the freezer mounted vacuum chamber and a vacuum of 26.5 Torr was applied for eight hours and then the cob was allowed to sit in the silicone fluid in the freezer for twelve hours without any additional vacuum being applied.

Thereafter, the silicone fluid was carefully decanted from the beaker and the cob was removed and allowed to drain to remove excess liquid for about two minutes. The cob was then placed in a clean beaker and ethyltrimethoxysilane as a crosslinker was added in an amount to submerge the cob. The beaker was then returned to the freezer mounted vacuum chamber and as before, a vacuum of 26.5 Torr was applied. Very few bubbles were noted and after eight hours, the application of a vacuum was discontinued and the cob was allowed to sit in solution in the freezer for an additional twelve hours.

A heated oven containing a chamber was used to heat the sample to 130° F. The heated oven consisted of the oven, containing a chamber inside wherein the chamber was essentially a polypropylene pail with a tight fitting lid which was inverted in the oven and laid on the bottom surface of the oven. On the inside surface of the lid of the pail was placed a small petri dish and the petri dish was surmounted by a wire support screen onto which was placed the cob. The petri dish was used to contain the desired catalyst for the curing step of the process.

Two ounces of Fastcat 2003 catalyst was placed in the petri dish and the cob was subjected to the 130° temperature for a period of eight hours, at which time the cob was removed from the chamber and examined. The surfaces of the cob were slightly wet to the human touch. The catalyst was removed from the petri dish and two ounces of fresh catalyst was added to the dish. The cob was then placed in the chamber and subjected to an additional twenty-four hours at 130° and after checking the cob for cure, for an additional three days of treatment. At this point, pipe cleaners were saturated with the catalyst and the pipe cleaners were inserted into the core of the cob and the outside of the cob was treated by sprinkling the catalyst on a lint free rag, and wrapping the cob in the cloth whereupon the cob was allowed to sit in this fashion at room temperature for two days and then the cob was evaluated.

Comparisons were made between the cob treated by the process of this invention and several other cobs that had been air-dried from water-logged samples from the same provenance and time period. The initial observations indicated that extensive shrinkage and distortion destroyed the aesthetics of the cobs which were allowed to air-dry.

Very little particulate was noted in either the silicone liquid or the ethytrimethoxysilane after they were decanted following the treatment by each material. Post treatment measurements and weighing of the cob indicated that the process was very successful in preserving the original waterlogged artifact. The cob weighed 16.6 grams and measured 5.6 centimeters in length and 2.5 centimeters in diameter, by measuring the same point on the cob from which the original measurements had been taken. The cob thus changed in weight by −1.2% and only diminished by −5.2% in diameter. The post treatment length of the cob remained the same as the wet length of the cob when first measured. A comparison can be made by reference to TABLE I, below.

The cob is darker in color than the coloration of most of the corn cobs, no attempts were made at removing stains and discoloration which may have been caused by the long time close association of the artifact to sediments and other decomposing materials.

TABLE I

| SAMPLE | WEIGHT/GRAMS | LENGTH/Cm | WIDTH/Cm |
| --- | --- | --- | --- |
| Original wet dimensions | 16.80 | 5.60 | 2.63 |
| Post treatment dimensions | 16.60 | 5.60 | 2.50 |
| Percentage Change | −1.2048% | 0.0% | 5.20% |

EXAMPLE 2

Preservation of Artifacts: Cork

Six waterlogged corks from the 1692 provenance of excavations at Port Royal, Jamaica were used in this experiment. Three different siloxane liquids were used in this experiment, namely polydimethylsiloxanes having hydroxy groups on each end of the molecule and having molecular weights of A=9000, B=2700, and C=550 g/mole, respectively. Before treatment, all six corks had been stored in a polyethylene bag in fresh tap water and all of the corks were removed from the bag and placed in a large vat and rinsed with running water for two days. All of the corks were photographed, and their configurations were drawn on paper for later comparison. All of the corks were weighed and their dimensions measured and the same was recorded. This information is found in TABLE IIA.

TABLE IIA

| | WET | | | |
|---|---|---|---|---|
| SPECIMEN | WEIGHT/ gms. | LENGTH/cm. | WIDTH/cm. | TREATMENT |
| 1 | 10.5 | 3.60 | 2.13 | air-dry |
| 2 | 6.7 | 2.83 | 1.73 | Siloxane A |
| 3 | 6.7 | 2.84 | 1.95 | Siloxane B |
| 4 | 5.0 | 2.86 | 1.66 | Siloxane B |
| 5 | 6.5 | 3.09 | 1.73 | Siloxane A |
| 6 | 4.0 | 2.64 | 1.62 | Siloxane C |

One cork was left to air dry and was labeled specimen 1. The remainder of the corks were placed in a bath of acetone to dehydrate them. The beaker containing the acetone and corks was placed in a freezer mounted vacuum chamber and a vacuum of minus 26.5 Torr was applied for eight hours. The acetone was decanted and fresh acetone was added to the corks and this was stored in the freezer for 12 hours.

Separate beakers were filled each with Siloxane A, Siloxane B, and Siloxane C and the corks immersed therein and they were weighted to keep them submerged. A vacuum of 26.5 Torr was applied to all of the samples for five hours and the samples were allowed to sit with the vacuum off for twelve hours in the freezer. Then, all of the corks were removed and placed in a cotton bag and the bag containing the corks was immersed in methylhydrogencyclosiloxane as a crosslinker. A vacuum of 26.5 Torr was applies for one hour and then the corks were removed and placed individually in an oven at 135° F. which contained a tray of Fastcat 2003 catalyst. They were held for two days and then they were allowed to stand for 24 hours. The corks were then remeasured and reweighed and the results can be found on TABLE IIB.

TABLE IIB

| SAMPLE | WEIGHT CHANGE/% | LENGTH CHANGE/% | WIDTH CHANGE/% |
|---|---|---|---|
| 1 | −90.6 | −27.8 | −15.5 |
| 2 | −55.2 | −4.6 | 00.0 |
| 3 | −43.3 | −15.5 | −5.1 |
| 4 | −21.0 | −14.3 | −3.6 |
| 5 | −69.2 | −9.4 | 00.0 |
| 6 | −50.0 | −13.6 | −10.5 |

EXAMPLE 3

In order to determine if the curable siloxane systems would cure in wooden artifacts, experiments were carried out on fresh wood to determine the effects of the system.

Thus, six samples of finely ground sawdust were prepared by mixing the 2 grains of the sawdust with 6.6 grams of the polymer of example 4. These samples were labeled as 1A, 1B, 1C, 1D, 1E, and 1F. Nine additional samples, each containing an additional 3 weight percent of methyltrimethoxysilane were also prepared and these were labeled 2A, 2B, 2C, 2D, 2E, 2F, 3B, 3D, and 3F.

Sample numbers, catalyst types, chamber types and results can be found on TABLE III.

TABLE III

| SAMPLE # | CATALYST | CHAMBER | RESULT |
|---|---|---|---|
| 1A | Tin Octoate | O | 1 |
| 1B | " | C | 1+ |
| 1C | DBTDA | O | 1+ |
| 1D | " | C | 2 |
| 1E | TPT | O | 1+ |
| 1F | " | C | 5 |
| 2A | Tin Octoate | O | 1+ |
| 2B | " | C | 2 |
| 2C | DBTDA | O | 1+ |
| 2D | " | C | 5 |
| 2E | TPT | O | 1+ |
| 2F | " | C | 5 |
| 3B | Tin Octoate | Glass/C | 1+ |
| 3D | DBTDA | " | 1+ |
| 3F | TPT | " | 2 |

Table III Key
The results of 1 to 5 have the same meaning as in TABLE 5.

Six waterlogged tongue depressors that had been in contact with water for about 10 years, were dehydrated in acetone in a freezer mounted vacuum chamber and then placed in a solution of siloxane fluid mixed with about 3 weight percent methytrimethoxysilane. The impregnation was conducted for about 24 hours and then the samples were placed in a glass containment chamber for catalyst treatment using dibutyltindiacetate.

When finished, microscopy of thin cross sections of the finished samples indicated that these samples had been successfully bulked (conserved) with the curable siloxane system. Tongue depressors that had not been treated as above, but were allowed to air dry, were warped and underwent extensive shrinkage when dried. The treated tongue depressors retained the same features as the untreated control tongue depressors, that is tongue depressors that were not waterlogged, and the siloxane treated tongue depressors were generally slightly darker in color than untreated control tongue depressor samples.

EXAMPLE 4

Experiments were carried out on leather to determine if leather would assume the impregnation to the extent that the process would be valuable for impregnating artifactual leather.

Six samples of fresh untreated (i.e. non-tanned) cow hide were dehydrated in the freezer mounted vacuum chamber using acetone. Three samples were then subjected to a curable siloxane system consisting of siloxane 2, combined with about three weight percent of methyltrimethoxysilane. One each of the three samples was subjected, respectively, to dibutyltindiacetate, tin Octoate, and tetraisopropyltitanate in closed, individual chambers and one each of the three additional samples were placed in open containment chambers with each of the three catalysts.

It was noted that the samples treated in the open ended containment chambers were considerably harder than their counterparts treated in the closed containment chambers. The samples treated in the closed containment chambers remained more supple. All samples were essentially wholly impregnated.

A second set of pieces of semi-finished hides were dehydrated in acetone at room temperature for 18 hours at 28 inches of vacuum. The samples were then placed into fresh acetone in a 4 liter stainless steel beaker, and with a vacuum plate attached to the top of the beaker, the entire unit was placed in a freezer for 4 hours of FMVC treatment at 9.5 inches of vacuum. All of the sections were cut into approximately equal sizes measuring 1.5 inches by 1.75 inches in measurement. After dehydration, two pieces of hide were placed directly in a 500 milliliter solution of siloxane 2 with 3 weight % MTM added. After placing a small piece of aluminum mesh over the samples to prevent them from floating while processing, the samples were placed into a 4 liter stainless steel beaker. A vacuum plate was placed on the top of this beaker and then the entire assembly was placed into a freezer for FMVC processing at 9.5 inches of vacuum. The samples were removed from this solution after five hours of treatment and each was lightly wiped with paper towel to remove free flowing siloxane. The samples were then placed into one pint sized containment chambers, which were fashioned by inverting a polyethylene container with a tight fitting lid such that the lid of the unit acted as a flat base. Twenty grams of dibutyltindiacetate (DBTDA) were placed in the catalyst tray and then both samples were placed on a paper towel covered screen over the catalyst tray. The containment chamber was then placed in position over the samples and tightly closed. The entire assembly was then placed into a vented warming oven that had been set at 160° F., for 18 hours of vapor deposition. One of these samples was tested and it was designated sample "A". Three additional samples were treated in essentially the same way. These samples were designated "B", "C", and "D". Samples "E" and "F" were treated differently as can be found in TABLE IV below.

After treatment using dibutyltindiacetate as the catalyst, all of the samples were thin-sectioned for microscopic analysis. In all cases, the sections of bluestock had been thoroughly impregnated with the curable siloxane systems.

EXAMPLE 7

A piece of tanned and buffed cow hide was successfully impregnated with a curable siloxane system using the siloxane polymer of example 4 and using about three weight percent phenylmethyldimethoxysilane as a curing agent. The leather was lightly wiped with paper towel and then treated with dibutyltindiacetate in a small containment chamber.

EXAMPLE 8

A similar piece of leather was treated with a curable siloxane system which consisted of the siloxane of Example 13 catalyzed with 3% DBTDA.

EXAMPLE 9

A dog heart used in this experiment was about the size of a large chicken's egg in volume. After soaking the heart in cold running water for one hour, the heart was gently massaged for approximately five minutes while submerged in cold water to facilitate the removal of as much blood from the organ prior to treatment. After allowing the heart to drip dry of free flowing water for a few minutes, the heart was placed into 2 liters of fresh acetone and allowed to passively dehydrate in a covered container at room temperature for two days. The heart was then placed into a fresh bath of acetone and placed into a freezer for FMVC water/acetone displacement for 8 hours at 9 inches of vacuum.

The heart was then removed from the acetone bath and placed into a solution of siloxane 3 into which had been

TABLE IV

| SAMPLE | SILOXANE | CROSSLINKER | CATALYST | OBSERVATIONS | MICROSCOPY |
|---|---|---|---|---|---|
| A | Siloxane 6 | mtm | dbtda | Dry, slightly stiff, stress marks | Siloxane white throughout |
| B | Siloxane 5 | mtm | dbtda | dry, supple white stress marks | Siloxane white throughout |
| C | Siloxane 4 | mtm | dbtda | more supple than 2, slightly damp | Siloxane white throughout |
| D | Siloxane 2 | mtm | dbtda | supple but damp | Siloxane white throughout |
| E* | " | " | " | not as opaque as A–D | Siloxane white throughout** |
| F | Fresh hide, no treatment control sample | | | not as opaque as A–D | Siloxane white throughout |

*Fresh hide, 6 hours of FMVC
**more opaque than D

EXAMPLE 5

A bobcat pelt, consisting of the entire head and back pelt from the animal was acetone dehydrated at ambient pressure and room temperature and then preserved using a curable siloxane as in example 4. The pelt was successfully preserved.

EXAMPLE 6

Chromium-blue partially processed bluestock cowhides and finished buffed hides, were treated as in Example 4.

added 3 weight percent of MTM. The process of acetone/siloxane displacement was started at room temperature for a period of 2 hours, in a large vacuum chamber with a recorded vacuum of 28 inches. The organ in solution was then placed into a freezer mounted vacuum chamber for 18 hours of continuous processing at 9.5 inches of vacuum. The heart was left in solution at ambient pressure in the freezer for 16 hours and then acetone/siloxane displacement was continued for an additional 6 hours at 9.5 inches of vacuum. The heart was then removed from the freezer and allowed to stand at room temperature in the solution for 2 hours. The heart was then transferred into another container and submerged in a solution of siloxane (1) from example 13 which contained 3% MTM. The heart was then returned to the freezer for 4 hours of FMVC treatment at 9.5 inches. After the acetone/siloxane displacement process was completed, the heart was removed from the silicone oil and placed on a mesh screen, suspended over another large beaker. In this position, excess, free flowing siloxane was allowed to drip from the surfaces of the heart for one half hour. The heart was then surface wiped to remove areas of heavily pooled siloxane from its surfaces. Using a small eye dropper, four drops of DBTDA were inserted into the uppermost large open end of an artery, located at the top of the heart.

The heart was then placed into a large containment chamber, fashioned by placing a large polyethylene pail and its tight fitting lid in an inverted position. In this position, the lid of the unit acted as a flat base on which a catalyst tray and specimen could be placed. Centrally located on the base of the containment chamber, a flat tray containing three ounces of DBTDA was held in position using a small piece of double sided tape. A large piece of mesh screen was placed on top of this catalyst tray and its edges were folded over to firmly attach the screen to the sides of the catalyst tray. This screen acted as a platform on which the heart could be placed allowing it to be positioned directly over the fumes of catalyst during treatment. With body of the containment chamber placed in position and firmly sealed, the assembly was then placed in a vented warming oven set at 160° F. The catalyst treatment lasted for 24 hours and then the heart was removed form the oven, placed into a vented fume hood and left in it containment chamber for five days at room temperature. Total time for the conservation process was seven days, although it is believed that the process should not take more than 4 to 5 days at the most, under normal non-experimenting conditions.

After the treatment, the heart was cut in half using a long blade knife. Thin sections of tissue taken from the thickest areas of the wall of the heart were collected and microscopic analysis of the samples indicated that the deep tissues of the heart had been successfully impregnated and crosslinked with the siloxane. Aesthetically, the heart is very natural looking. Contrary to prior art methods used for preserving heart tissue, i.e. the Von Hagens process, the veins and arteries do not need to be especially dye colored since the inventive process appears to maintain the red coloration of blood within the vessels of the tissue.

EXAMPLE 10

Several pig hearts were placed in a large container of fresh, cold water which was connected to the container such that fresh water was pumped through the container continually. Additionally, the water was aerated such that it aided in the cleansing and removal of much of the blood remaining in the hearts. Aerated soaking continued for twenty four hours at room temperature. After cleaning, six of the hearts were stored in a water bath in a freezer. The remaining two hearts labelled samples 1 and 2 were FMVC treated in fresh acetone for 48 hours at 9.0 inches of vacuum. After this step, the hearts were removed from FMVC treatment and placed into a fresh bath of acetone. Passive dehydration continued for an additional 48 hours at room temperature. Sample 1 was removed from acetone and placed into a 4 liter stainless steel beaker containing 2 liter of siloxane 2, which had 3% MTM added to it. The assembly of the equipment was similar to that found in Example 16. A vacuum plate was placed over the top of the stainless steel beaker and after securing, the entire assembly was placed into a freezer for 58 hours of FMVC processing at 9.5 inches. The heart was left in solution sitting in the freezer at ambient pressure for 5 hours.

Sample 1 was then removed from the FMVC assembly and placed on a section of screen, sitting over a large container. In this position, the heart was allowed to drain of the free flowing siloxane for a short period of time and then the surfaces of the heart were wiped lightly with paper towel. Sample 1 was then placed into a large beaker containing 500 ml. of fresh MTM and moved around in the solution for approximately one minute. After this step, the heart was removed from the MTM and allowed to sit on paper towel until the containment chamber was prepared. At this time, the sample was wiped with paper towel that had been moistened with a few drops of DBTDA. Care was taken to ensure that all exterior surface of the heart had been wiped with the catalyst.

The containment chamber was set up as in the previous example. Thirty grams of DBTDA was placed in the catalyst tray. The containment chamber was then placed in a vented warming oven that had been set to 160° F. After 24 hours of vapor deposition, the sample was removed from the oven and thin sections cut from the thickest parts of the heart showing that these thick parts of the heart were not firm and had not been totally treated by the process. Fresh catalyst was added to the catalyst tray and this sample was returned to the chamber. The unit was returned to the oven for an additional 48 hours of catalyst vapor deposition. The sample was removed from the oven and again, thin sections were taken for analysis. On evaluation, it was noted that there was an even distribution of cured silicone throughout the tissues of the heart. The heart appeared aesthetically nice and did not have any characteristic odor of decomposition.

Sample 2 was allowed to passively dehydrate for 168 hours in acetone at room temperature. It was then treated with water/acetone displacement for 6 hours using FMVC processing at 15 inches vacuum. The sample was then removed from the FMVC assembly and placed into a 4 liter stainless steel beaker containing siloxane 2 and 3% MTM and 0.1 weight % of DBTDA. The sample was then subjected to the FMVC process for 19.5 hours. The sample was then removed and drained of the siloxane fluid. It was then dipped into fresh MTM for two minutes and moved about in the MTM. It was allowed to drain and then placed into the containment chamber and 3 ounces of DBTDA placed in the catalyst tray. The entire assembly was then placed into the oven at 160° F.

It was left there for approximately eight days to ensure the deep section cure. Under microscopic evaluation, it was evident that the deep tissues of the heart had been successfully impregnated and cured. There was no odor of degradation.

A third pig heart was initially placed into a 4 liter stainless steel container and placed into FMVC water/acetone displacement for 48 hours passive treatment. The heart then received an additional 16.5 hours of FMVC treatment at 2.0 inches of pressure. The heart was then removed from the freezer and placed into 2 liters of fresh acetone where it was allowed to continue passive dehydration in room temperature acetone for 48 hours. The acetone was replaced daily so that through the two day period of dehydration at room temperature, the acetone was changed once.

This heart, sample 3, was then removed from the water/acetone displacement and placed directly into a stainless steel beaker containing 2 liters of siloxane 2 with 3 weight % MTM added thereto. The heart was weighted down with a section of mesh screen and a small weight and a vacuum plate was attached to the top of the beaker and the entire assembly was placed into a freezer for FMVC acetone/siloxane displacement at 2.0 inches of vacuum. The heart remained in treatment for 9 hours at 9.0 inches of vacuum.

The heart was then removed from the siloxane and placed on a section of mesh so that free flowing siloxane could drip from the surface. The surface was wiped gently with a paper towel. DBTDA was then applied to the surface by hand, using a cotton glove covering a rubber glove and the heart was massaged to cover all of the crevices and irregularities of the surface. In addition, DBTDA was placed in the catalyst try and the heart was treated by sealing the chamber and warming the oven for 6 days at 160° F.

Upon removal from the oven, the heart had a firm texture and microscopic analysis of several thin sections indicated that the heart was completely preserved.

EXAMPLE 11

A pig heart, designated "B" was dehydrated in acetone for 48 hours in the freezer mounted vacuum chamber. This was followed by two days of passive acetone dehydration at ambient pressure and room temperature. Fresh acetone was then placed in the stainless steel container and the heart remained in passive dehydration for an additional 168 hours and then the organ was further dehydrated in acetone using freezer vacuum for an additional six hours. It was then treated with a curable system using the system set forth in example 4. The heart was drained of free-flowing solution, placed in methyltrimethoxysilane for two minutes and then treated with dibutyltindiacetate in a conventional containment chamber set-up. It was treated for eight days. Microscopic investigation showed that the heart had been thoroughly conserved by the cured siloxane system.

EXAMPLE 12

A third pig heart, designated "C" was treated with extensive acetone dehydration prior to conservation. Then the heart was treated to 48 hours of freezer mounted vacuum chamber dehydration followed by two days of sitting in acetone in the freezer at ambient pressure. The heart was then placed in fresh acetone and allowed to sit at ambient pressure and room temperature for an additional two days. After treating with a curable siloxane system as in example 4, for thirty three hours, the heart was removed from the solution and the surface wiped with paper towel. Dibutyltindiacetate was then massaged into the surfaces and crevices of the heart. After six days of this treatment, the heart was completely conserved.

EXAMPLE 13

Preservation of Old Paper

Pages of a very old book which were yellowed and brittle were crumpled by hand and then placed into a common blender and reduced to a fine consistent powder.

Six samples were prepared, each containing 7.0 gms. of Siloxane 2 and 1.25 gms. of the crumpled paper. These samples were labeled 1A, 1B, 1C, 1D, 1E, and 1F. Eight additional samples, each containing 7.0 gms. of the siloxane fluid and 3 weight % methyltrimethoxysilane and 1.25 gms. of paper were mixed in individual aluminum trays. These were labeled as 2A, 2B, 2C, 2D, 2E, 2F, and 3B, and 3D.

Identical containment chambers, like those used in previous experiments illustrated above, were used for this experiment. Thus, individual containment chambers were created for this experiment using one pint polyethylene cups with tight fitting lids. In an inverted position, the lid formed a flat base with the body of the container acting as a lid. Two one quart jars were used as containment chambers for samples 3B and 3D. Placement of catalyst and sample trays was done exactly the same as in the previous examples. Other than material composition, the volume with the glass chambers was double that of the polyethylene cups. A small piece of double sided tape was used to secure an aluminum sample tray to the base of the unit. In this tray, the designated catalyst for the sample being tested was placed. A piece of open mesh screen, measuring approximately 1.75 inches square was then placed over the aluminum tray and its edges were folded over to secure the screen on top of the catalyst tray. This screen acted as a mounting platform upon which an aluminum tray holding the sample being tested was placed. In this position, the sample was directly above the catalyst tray, minimizing any splashing that might occur while placing the containment chamber in the warming oven. With the body of the containment chamber in place, all samples were then placed into a vented warming oven which had been set at 70° C. Vapor deposition continued in this oven for 48 hours. The results are listed below in TABLE V.

TABLE V

| SAMPLE | TREATMENT | CATALYST | CHAMBER TYPE | RESULTS |
|---|---|---|---|---|
| 1A | Siloxane 2 | Sn (Oct)$_2$ | Op | 1 |
| 1B | Siloxane 2 | " | C | 1 |
| 1C | Siloxane 2 | DBTDA | Op | 2 |
| 1D | Siloxane 2 | " | C | 2+ |
| 1E | Siloxane 2 | TPT | Op | 1 |
| 1F | Siloxane 2 | " | C | 1 |
| 2A | Siloxane 2 + MTM | Sn (Oct)$_2$ | Op | 2 |
| 2B | Siloxane 2 + MTM | " | C | 4+ |
| 2C | Siloxane 2 + MTM | DBTDA | Op | 3 |
| 2D | Siloxane 2 + MTM | " | C | 5 |
| 2E | Siloxane 2 + MTM | TPT | Op | 4+ |
| 2F | Siloxane 2 + MTM | " | C | 5 |
| 3B | Siloxane 2 + MTM | Sn (Oct)$_2$ | G/C | 2+ |
| 3D | | DBTDA | G/C | 2+ |

TABLE V KEY
MTM = Methyltrimethoxysilane
DBTDA = dibutyltindiacetate
TPT = tetraisopropyltitanate
Op = open, where the top of the jar was left open inside of the containment chamber.
C - closed, where the top of the jar was closed inside of the containment chamber.
G/C = glass container, closed
O = no change in the material.
1 = some thickening of the material
2 = very thick, some gellation
3 = very thick, light crosslinking, some crusting
4 = very nearly cured, slightly tacky
5 = totally cured, solid, non-tacky

EXAMPLE 14

Conservation of Glass

Experiments using glass as the substrate were carried out using the same methodologies as were used for the paper above.

Panes of glass were placed in a plastic bag and hammered until the glass was reduced to very small particles. The particles were then placed into a blender and by using the pulse button, the particles were reduced to a very fine glass particle. The ratio of glass to the treatment material was 15 grams of glass to 3.55 of the treatment material which consisted of the same materials in the same ratios as was used in Example 13.

The results can be found in TABLE VI.

TABLE VI

| SAMPLE | TREATMENT | CATALYST | CHAMBER TYPE | RESULTS |
|---|---|---|---|---|
| 1A | Siloxane 2 | Sn(Oct)$_2$ | Op | 1+ |
| 1B | Siloxane 2 | " | C | 4+ |
| 1C | Siloxane 2 | DBTDA | Op | 1+ |
| 1D | Siloxane 2 | " | C | 4+ |
| 1E | Siloxane 2 | TPT | Op | 1+ |
| 1F | Siloxane 2 | " | C | 5 |
| 2A | Siloxane 2 + MTM | Sn(Oct)$_2$ | Op | 1+ |
| 2B | Siloxane 2 + MTM | " | C | 7 |
| 2C | Siloxane 2 + MTM | DBTDA | Op | 5+ |
| 2D | Siloxane 2 + MTM | " | C | 7 |
| 2E | Siloxane 2 + MTM | TPT | Op | 2 |
| 2F | Siloxane 2 + MTM | " | C | 5 |
| 3B | Siloxane 2 + MTM | Sn(Oct)$_2$ | G/C | 6 |
| 3D | Siloxane 2 + MTM | DBTDA | G/C | 5+ |
| 3F | Siloxane 2 + MTM | TPT | G/C | 6 |

MTM = Methyltrimethoxysilane
DBTDA = dibutyltindiacetate
TPT = tetraisopropyltitanate
Op = open, where the top of the jar was left open inside of the containment chamber.
C - closed, where the top of the jar was closed inside of the containment chamber.
G/C = glass container, closed
O = no change in the material.
1 = some thickening of the material
2 = very thick, some gellation
3 = very thick, light crosslinking, some crusting
4 = thick top layer, very wet underneath
5 = solid top layer, wet underneath
6 = very nearly cured, solid and tacky
7 = totally cured, solid and non-tacky

EXAMPLE 15

Conservation of Onion Bottle Glass

This experiment was carried out on waterlogged, devitrified archaeological glass which was recovered from excavations of the 1692 provenance of Port Royal, Jamaica.

The glass was in fragments and these fragments were taken from a section of broken bottle which are commonly called onion bottles. These bottles are found in abundance at the Port Royal site. When recovered from excavations at the sites, care must be taken to keep these bottles wet during transport to the lab and during curation in preparation for conservation. If allowed to air dry, it is not uncommon to see large layers of flakes exfoliate from the surfaces to the bottles, much like removing layers from an onion. If left to dry, an intact bottle can be reduced to rubble in a short period of time.

Before treatment with the siloxanes, all samples of glass were placed into a large stainless steel beaker and immersed in one liter of fresh acetone. The samples were then dehydrated in a freezer mounted vacuum chamber for four hours at a high vacuum. The glass was then removed from the acetone and placed into a 200 gram solution of siloxane 2, to which 3 weight percent of methyltrimethoxysilane was added. The samples in solution were then placed in a freezer and a vacuum plate was placed over the stainless steel beaker. Acetone/silicone solution displacement was conducted on this these samples for six hours under vacuum. After this treatment, the glass samples were removed from the siloxane mixture and gently blotted with paper towel to remove most of the free flowing and surface pooled liquid.

The samples were then subjected to catalyst vapors according to the apparatus and procedures as set forth in Example 13. Thirteen gms. of dibutyltindiacetate were placed in the catalyst tray for these experiments and the containment chamber was heated to about 160° F. and the samples were left therein for about sixteen hours. TABLE VII lists the treatments for samples 1 through 3.

TABLE VII

| SAMPLE | TREATMENT | CATALYST |
|---|---|---|
| 1 | siloxane 2 + 3% MTM | DBTDA |
| 2 | siloxane 5 + 3% MTM | " |
| 3 | siloxane 4 + 3% MTM | " |

Several additional samples of glass were prepared. The process for sample 4 was modified in that after acetone dehydration, the sample was removed from acetone and placed directly into a container of MTM with a sufficient amount to submerge the glass sample totally. The sample in solution was then placed into a large stainless steel beaker and after placing a vacuum plate over the beaker, a vacuum was applied for six hours. After this treatment, the glass was lightly surface blotted with paper towel. After blotting, the sample was placed into an individual containment chamber identical to the type described above. The sample was then placed along side the other samples in the vented warming oven for 16 hours at 160° F.

Sample 5 was not acetone dehydrated prior to treatment. The sample was rinsed in fresh running water and then submerged in a beaker of fresh MTM. The beaker containing the sample in solution was placed into a four liter stainless steel beaker and after a vacuum was applied, the entire assembly was placed inside a freezer for six hours.

After this treatment, the sample was left in the freezer in solution and at ambient pressure for approximately 18 hours and then subjected to the catalyst vapor for twenty-four hours at 160 degrees F.

Sample 6 consisted of four small samples of glass. These samples were rinsed in running tap water for approximately one hour and then placed directly into 200 grams of siloxane 3 from above in which there was present 3% MTM. These samples were then placed in a freezer mounted vacuum chamber and treated in solution for six hours under vacuum.

After this treatment, the samples were left in solution in the freezer at ambient pressure for approximately eighteen hours. The samples were removed from the siloxane mixture and lightly patted with paper towel to remove free flowing surface solution. The samples were then placed into the same configuration of containment chamber was used in the previous Examples. The samples were subjected to catalyst vapor as above, for 24 hours at 160° F.

The samples were subjectively evaluated for clarity of glass, overall aesthetics, presence or absence of a "rainbow" discoloration or filminess on the surface of the glass and overall integrity of the samples. The results can be found on TABLE VIII.

TABLE VIII

| SAMPLE | INITIAL EVALUATION | 24 HOUR EVALUATION |
|---|---|---|
| 1 | slightly tacky, glossy, to semi-glossy, no flaking, aesthetically good | Good overall |

TABLE VIII-continued

| SAMPLE | INITIAL EVALUATION | 24 HOUR EVALUATION |
|---|---|---|
| 2 | dry, glossy to semi-glossy, good color, oxides on glass are consolidated | Very good overall |
| 3 | surface not uniformly coated, some pooled and cured siloxane, not aesthetically pretty | Reasonably good |
| 4 | dry, clear, aesthetically good | to Excellent overall |
| 5 | rainbow coloration, opaque layer noted, dead glass appearance, poor | Very poor |
| 6 | slight rainbow coloration, glass not flaking, surface appears stable | Reasonable appearance |
| 7 | uniform glass color, material is well consolidated | Good to Excellent |

EXPERIMENT 16

Preservation of Fish

Sample experiments were carried out to try to preserve fish using small goldfish. It appeared that the use of vacuum during the processing did not lend itself well to the preservation of the goldfish because it was observed that the fish were too fragile for the vacuum treatment and essentially split and otherwise came apart.

Therefore, the procedure was modified. Two goldfish specimens were subjected to long term passive dehydration. These fish were stored in fresh acetone for two months at room temperature and ambient pressure. After dehydration, the specimens were placed into the siloxane 3 containing MTM. The fish were weighted down so that the solution covered them. They were treated in this manner for 2 hours at room temperature. Then vacuum was increased slowly over the first thirty minutes of treatment, ultimately reaching a vacuum of 28 inches. The samples were then transferred to a freezer for 1 hour of FMVC treatment. The samples were left in solution in the freezer at ambient pressure over the weekend. The samples were retreated using the FMVC process for an additional 7.5 hours at 2 inches of vapor pressure. The samples were then removed from the freezer and solution and lightly patted on the surface with paper towel. Sample 1 was then placed into a small containment chamber using the same methodologies as was used for the Example 13 samples. With 20 grams. of DBTDA in the catalyst tray, the sample was sealed in the container and then the sample was placed into a vented warming oven set at 160 degrees F. for 18 hours.

Sample 2 was removed from the siloxane mixture and after lightly patting the surface with a towel, the sample was mounted onto a small containment chamber. Twenty grams of tin dioctoate were used for the catalyst. This treatment was carried out for 18 hours. After this treatment, both samples were removed from the oven and allowed to sit for 24 hours.

Sample 1 was totally dry and aesthetically pleasing. The skin texture of the fish and the fine details of the fins were all well preserved. Sample 2 was equally well preserved although there was a slight blemish or blotchy appearance on one side of the finished specimen. The samples were both very natural looking and appeared to be well preserved.

EXAMPLE 17

This is an example of a silane crosslinker having both alkoxy and acyloxy substituents on the silicon atom to give mixed groups on the silicon atom. The silane crosslinker was prepared by adding in 25 gm increments, reagent grade isopropanol to 225 gms of Methyltriacetoxysilane which had been placed in an open top pint glass jar. The addition of the isopropanol creates a slight exotherm, and the lower one third of the glass jar was immersed in ice water to cool it. After the addition was complete, the jar was capped and it was allowed to stand several hours to complete the formation of the mixed crosslinker.

A sample 1 was prepared. It consisted of a corn cob which had been excavated from the Yorktown ship wreck which was subjected to the process described herein. Thus, the corn cob was subjected to room temperature vacuum in a vacuum chamber while sitting in fresh acetone for 7 hours, at which point, the rapid bubbling observed from the sample diminished to nothing. The corn cob was then placed into a hydroxy functional linear polydimethyl silicone polymer having about 100 dimethyl units which contained about 7 weight percent of the crosslinker prepared just above.

A screen was placed on top of the object to prevent floating in the acetone and subsequently in the immersion in the silicone solution. The sample and the solution was then subjected to vacuum in a vacuum chamber for 7.5 hours at a maximum vacuum of 4 mm. The sample was removed at that time and placed onto aluminum screen and allowed to drip free of free-flowing silicone solution and the sample was then placed in a fume hood and allowed to autocatalyze. Note that no catalyst was added to this procedure.

A second sample was treated as above, but at the end of the drip free step of the process, the sample was patted dry with paper towels, and then with a lint free cloth. The sample was then coated with dibutyltindiacetate topically applied with Q-tips to all exposed surfaces. Excess silicone solution, if any, and excess DBTDA was lightly blotted after letting the sample sit for approximately 5 minutes in the open air.

The sample 1 after curing at room temperature for about 12 hours, did not shown any significant shrinkage. It was slightly tacky to the touch with a small amount of distortion noted around the middle girth. It had a small amount of rippling to the surface but otherwise had a natural corn cob look to it.

Sample 2 had broken approximately in half during the process. There was no significant distortion and the sample was dry to the touch after 12 hours of cure at room temperature in ambient air. Sample was heavily coated as compared to sample 1 as no effort had been made to blot the sample before treating with the DBTDA because of the rapid polymerization or crosslinking of the silicone materials. The sample did not have any surface rippling and appeared natural. Also, this sample is more firm than sample 1.

EXAMPLE 18

An additional mixed crosslinker was prepared bad adding 100 gms of octanoic acid to 100 gms of methytriacetoxysilane and 0.4 gms of DBTDA. This solution was allowed to sit one week in a closed jar before using.

Sample 1 consisted of a corn cob with the archival number AS195. This corn cob was very fragile. A second sample which had been identified as AS241, i.e. the "long cob" were both placed in acetone and a vacuum was pulled for 3.5 hours, that is until no bubbles could be seen emanating from the solution. Both cobs remained in the vacuum chamber overnight (12 hours) without additional vacuum being applied.

The first sample, which had broken into smaller pieces, was immersed in a mixture of 168 gms of hydroxyl endblocked polydimethylsiloxane having a degree of polymerization of about 100 and 14 gms of the cross-linker prepared just above. The mixture thickened quickly.

The second sample was placed in a solution of 279 gms of the siloxane polymer and 21 gms of the crosslinker, the additional amount of solution being needed to totally immerse the long section of corn cob.

Both samples were held into the solution by several wire-mesh restraints. A vacuum was drawn and the sample began to evolve bubbles. The vacuum was shut off and the vacuum released. The samples were removed from the solution and were already polymerizing such that the samples could not be blotted. The samples cured after a short time. There was little or no distortion to either of the samples and neither of the samples had shrunk. The coloration was good and the surfaces were heavily coated because of the fast polymerization.

What is claimed is:

1. A method of conserving organic and inorganic materials comprising impregnating an organic material or an inorganic material with a curable polymeric system comprising (i) a siloxane polymer having an average of at least two unsaturated groups per molecule, (ii) sufficient of a crosslinker to crosslink a significant portion of the siloxane polymer, the crosslinker comprising an organosilicon compound having at least two hydrogens on silicon, and which is selected from the group consisting of (a) a silane, (b) a siloxane, and (c) a mixture of (a) and (b), (iii) a platinum catalyst, and thereafter allowing the impregnated material to cure.

2. A method of configuring wood products comprising impregnating wood products with a curable system, configuring the wood products to a desired shape, maintaining the impregnated and configured wood product in its desired shape, and curing the curable system; the curable system being (i) a siloxane polymer having an average of at least two unsaturated groups per molecule, (ii) sufficient of a crosslinker to crosslink a significant portion of the siloxane polymer, the crosslinker being an organosilicon compound having at least two hydrogens on silicon selected from the group consisting of (a) silanes, (b) siloxanes, and (c) mixtures of (a) and (b), and (iii) a platinum catalyst.

* * * * *